(12) United States Patent
AlZoebi (10) Patent No.: US 11,638,630 B1
(45) Date of Patent: May 2, 2023

(54) SYSTEM AND PROCESS AND FOR REPLICATING SOFT TISSUE ANATOMY USING A FOR IMPLANT SUPPORTED FIXED PROSTHESES USING 3D PRINTED MULTI-PURPOSE PROTOTYPE

(71) Applicant: Kuwait University, Safat (KW)

(72) Inventor: Fawaz AlZoebi, Kuwait (KW)

(73) Assignee: Kuwait University, Safat (KW)

( * ) Notice: Subject to any disclaimer, the term of this patent is extended or adjusted under 35 U.S.C. 154(b) by 0 days.

(21) Appl. No.: 17/938,137

(22) Filed: Oct. 5, 2022

(51) Int. Cl.
*A61C 8/00* (2006.01)
*G16H 20/40* (2018.01)

(52) U.S. Cl.
CPC ........... *A61C 8/0001* (2013.01); *G16H 20/40* (2018.01)

(58) Field of Classification Search
CPC ............ A61C 13/0001; A61C 13/0024; A61C 13/0025; A61C 8/0001; A61C 8/00; A61C 8/0006; A61C 8/0048; A61C 8/008; A61C 8/0095; A61C 9/00
See application file for complete search history.

(56) References Cited

U.S. PATENT DOCUMENTS

2018/0250102 A1* 9/2018 Schulter ................. A61C 1/084
2019/0105134 A1* 4/2019 Cohen .................... B33Y 80/00

* cited by examiner

*Primary Examiner* — Amy R Sipp
*Assistant Examiner* — Sydney J Pulvidente
(74) *Attorney, Agent, or Firm* — Schott, P.C.

(57) ABSTRACT

A process for replicating soft tissue anatomy of a dental patient prior to preparing an implant-supported fixed prosthesis is disclosed. The process may include: securing an interim prosthesis intra-orally in the dental patient for a predetermined time, after implants of the dental patient are osseointegrated, to evaluate the interim prosthesis based on a plurality of parameters within the mouth of the dental patient; printing a three-dimensional printed-resin prototype having an intaglio surface based on the evaluated interim prosthesis; attaching the three-dimensional printed-resin prototype into the implants; and injecting a low viscosity elastomeric impression material between the intaglio surface of the three-dimensional printed-resin prototype and the soft tissue of the dental patient to obtain a soft tissue replica for preparing the implant-supported fixed prosthesis.

20 Claims, 14 Drawing Sheets

SYSTEM AND PROCESS AND FOR REPLICATING SOFT TISSUE ANATOMY USING A FOR IMPLANT SUPPORTED FIXED PROSTHESES USING 3D PRINTED MULTI-PURPOSE PROTOTYPE

FIELD OF INVENTION

The present invention relates to soft tissue anatomy replication in dentistry, and, more particularly, to a process and system for soft tissue anatomy replication for implant-supported fixed prosthesis using a 3D printed-resin prototype.

BACKGROUND OF THE INVENTION

Rehabilitation of completely edentulous patients with implant-supported fixed complete dentures (ISFCD) is a well-documented and predictable option to restore the aesthetics and function of the dental prosthesis. Currently, the use of computer-aided designing and manufacturing (CAD/CAM) facilitates the process to create ISFCD and improves the execution of such a treatment modality. The computer-aided designing and manufacturing of prostheses in dentistry with different material choices, such as zirconia, has increased in recent years in dentistry.

Although the benefits of using the zirconia for ISFCDs have been reported, one relatively significant drawback of the zirconia is the difficulty of adjusting the prosthesis in an oral cavity after fabrication, as such an adjustment may induce damage and/or compromise the material's strength. Such damage in some cases may require extreme measures, such as re-fabrication of the prosthesis. Hence, accurate replication of the clinical scenario and communication with the laboratory is crucial, especially when the zirconia is considered for use in the prosthesis.

Hence, fabricating a prototype prosthesis is considered important to facilitate workflow and assure proper replication of clinical scenarios in ISFCD. The fabricated prototype of a prosthesis is a duplication of what the clinician plans to fabricate and deliver as a final prosthesis. Such a fabricated prototype may be used to assess almost all parameters associated with ISFCD, such as maxillomandibular relationship, occlusion, teeth setup, phonetics, and aesthetics.

Hence, providing a temporary or a prototype prosthesis is important in ISFCD cases to assess functional and aesthetic parameters before committing to a final restoration. It is generally advised to have the temporary prosthesis functioning for at least six weeks to gain feedback and assure acceptable parameters. After delivery of the temporary prosthesis (whether immediately after implant placement or after a healing period), changes in the soft tissue are expected. Such changes in the soft tissue are due to normal healing patterns associated with post-surgery or due to pressure against an intaglio surface of the temporary prosthesis. Such dimensional changes in the soft tissue anatomy may significantly affect the accuracy of a master cast, especially if a delayed loading protocol is followed and if a final impression is acquired. Such changes, if not replicated on the master cast, may impact the accuracy of the fabrication of the final ISFCD.

Accordingly, there exists a need to provide a system and a process for replicating soft tissue anatomy for an implant-supported fixed prosthesis in dentistry that assures accurate replication of such changes and avoids conducting multiple final impressions.

SUMMARY OF THE INVENTION

A system and the process for replicating soft tissue anatomy for an implant-supported fixed prosthesis described herein overcomes the above drawbacks.

Accordingly, an object of the present invention is to provide accuracy in the fabrication of a final implant-supported fixed complete dentures (ISFCD).

Another object of the present invention is to provide a multi-purpose three-dimensional printed-resin prototype of a prosthesis, to capture details necessary to assure accurate replication of extra- and intra-oral features including soft tissue anatomy in dentistry.

In light of the above objects, in one aspect of the present disclosure, a process for replicating the soft tissue anatomy of a dental patient prior to preparing an implant-supported fixed prosthesis is disclosed. The process may include: securing an interim prosthesis intra-orally int o the integrated dental implants for a predetermined time in the patient for a predetermined time, to evaluate the interim prosthesis based on a plurality of parameters within the mouth of the dental patient; printing a three-dimensional printed-resin prototype having an intaglio surface based on the evaluated interim prosthesis; attaching the three-dimensional printed-resin prototype into the implants; and injecting a low viscosity elastomeric impression material between the intaglio surface of the three-dimensional printed-resin prototype and the soft tissue of the dental patient to obtain a soft tissue replica for preparing the implant-supported fixed prosthesis.

In another aspect of the present disclosure, a process for replicating a soft tissue anatomy of a dental patient prior to preparing an implant-supported fixed prosthesis is disclosed. The process may include: securing an interim prosthesis intra-orally in the dental patient for a predetermined time, after implants of the dental patient are osseointegrated, to evaluate the interim prosthesis based on a plurality of parameters in mouth of the patient; printing a three-dimensional printed-resin prototype with a predesigned 2 mm space between the intaglio surface and the soft tissue based on the evaluated interim prosthesis; attaching the three-dimensional printed-resin prototype into the implants; making an occlusal registration on a registration material, upon attaching the three-dimensional printed-resin prototype into the implants, and removing the registration material carrying the occlusal registration from mouth of the dental patient after setting of the occlusal registration; drying the three-dimensional printed-resin prototype after the occlusal registration; injecting a low viscosity elastomeric impression material between the intaglio surface of the three-dimensional printed-resin prototype and the soft tissue of the dental patient; detaching the three-dimensional printed-resin prototype from the implants after complete set-up of soft tissue replica on the low viscosity elastomeric impression material; securing the three-dimensional printed-resin prototype on a master cast; and repouring the soft tissue replica on the master cast allowing contours of the intaglio surface and emergence profile to fabricate the implant-supported fixed prosthesis based on the master cast.

In yet another aspect of the present disclosure, a system for preparing an implant-supported fixed prosthesis for a dental patient is disclosed. The system may include an intra-oral scanning (IOS) device, a design module application, a three-dimensional printer, and an elastomeric impression compound injecting module. The intra-oral scanning (IOS) device may be configured to scan an evaluated interim prosthesis to digitize the interim prosthesis. Further, the design module application may be configured to design a three-dimensional printed-resin prototype with an intaglio surface having 2 millimeters (mm) cutback from soft tissue of the mouth of the patient, based on the digitized interim prosthesis. Furthermore, the three-dimensional printer may be configured to print the three-dimensional printed-resin prototype along with the intaglio surface with the 2 mm cut-back from soft tissue. Moreover, the elastomeric impression compound injecting module may be configured to inject a low viscosity elastomeric impression material between the intaglio surface of the three-dimensional printed-resin prototype and the soft tissue in the mouth of the dental patient to obtain a soft tissue replica of the dental patient to prepare the implant-supported fixed prosthesis.

In all of the above aspects, the low viscosity elastomeric impression material may be injected between the intaglio surface of the three-dimensional printed-resin prototype and the soft tissue, may firstly include injecting the low viscosity elastomeric impression material between the intaglio surface of the three-dimensional printed-resin prototype and the soft tissue intra-orally in the patient, starting from one side on the buccal all the way to the contralateral side then around the distal end and alongside the palatal, to obtain the soft tissue replica. Thereafter, the low viscosity elastomeric impression material may be wrapped around on at least one site of the three-dimensional printed-resin prototype to stabilize the low viscosity elastomeric impression material over the three-dimensional printed-resin prototype, when the three-dimensional printed-resin prototype is detached from the mouth of the patient.

These elements, together with the other aspects of the present invention and various features are pointed out with particularity in the claims annexed hereto and form a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description taken in conjunction with the accompanying drawing, in which:

FIGS. 2A to 11 illustrate various stages of the process 10 or 10" as seen in FIGS. 1A and 1B, in accordance with an exemplary embodiment of the present disclosure.

Like reference numerals refer to like parts throughout the description of several views of the drawing.

DETAILED DESCRIPTION OF THE INVENTION

The following is a detailed description of embodiments of the invention depicted in the accompanying drawings. The embodiments are in such detail as to communicate the invention. However, the amount of detail offered is not intended to limit the anticipated variations of embodiments; on the contrary, the intention is to cover all modifications, equivalents, and alternatives falling within the spirit and scope of the present invention.

In the following description, numerous specific details are set forth in order to provide a thorough understanding of the embodiments of the present invention. It may be apparent to one skilled in the art that embodiments of the present invention may be practiced without some of these specific details.

Various terms as used herein are shown below. To the extent a term used, it should be given the broadest definition persons in the pertinent art have given that term as reflected in printed publications and issued patents at the time of filing.

The terms "a" and "an" herein do not denote a limitation of quantity, but rather denote the presence of at least one of the referenced items. Thus, for example, a reference to "a prosthesis" includes one or more prostheses.

The terms "having", "comprising", "including", and variations thereof signify the presence of a component.

The term "three-dimensional printed-resin prototype" used herein is a multi-purpose three-dimensional printed-resin prototype used in the dental industry for creating an implant-supported fixed prosthesis, which is also popular as implant-supported fixed complete dentures (ISFCD). For the sake of readability and conciseness of the present disclosure, the term "three-dimensional printed-resin prototype" may be referred to as "prototype".

Further, the term "low viscosity elastomeric impression material" may be referred to as "impression material" for the sake of readability and conciseness of the present disclosure.

Figure 1A:
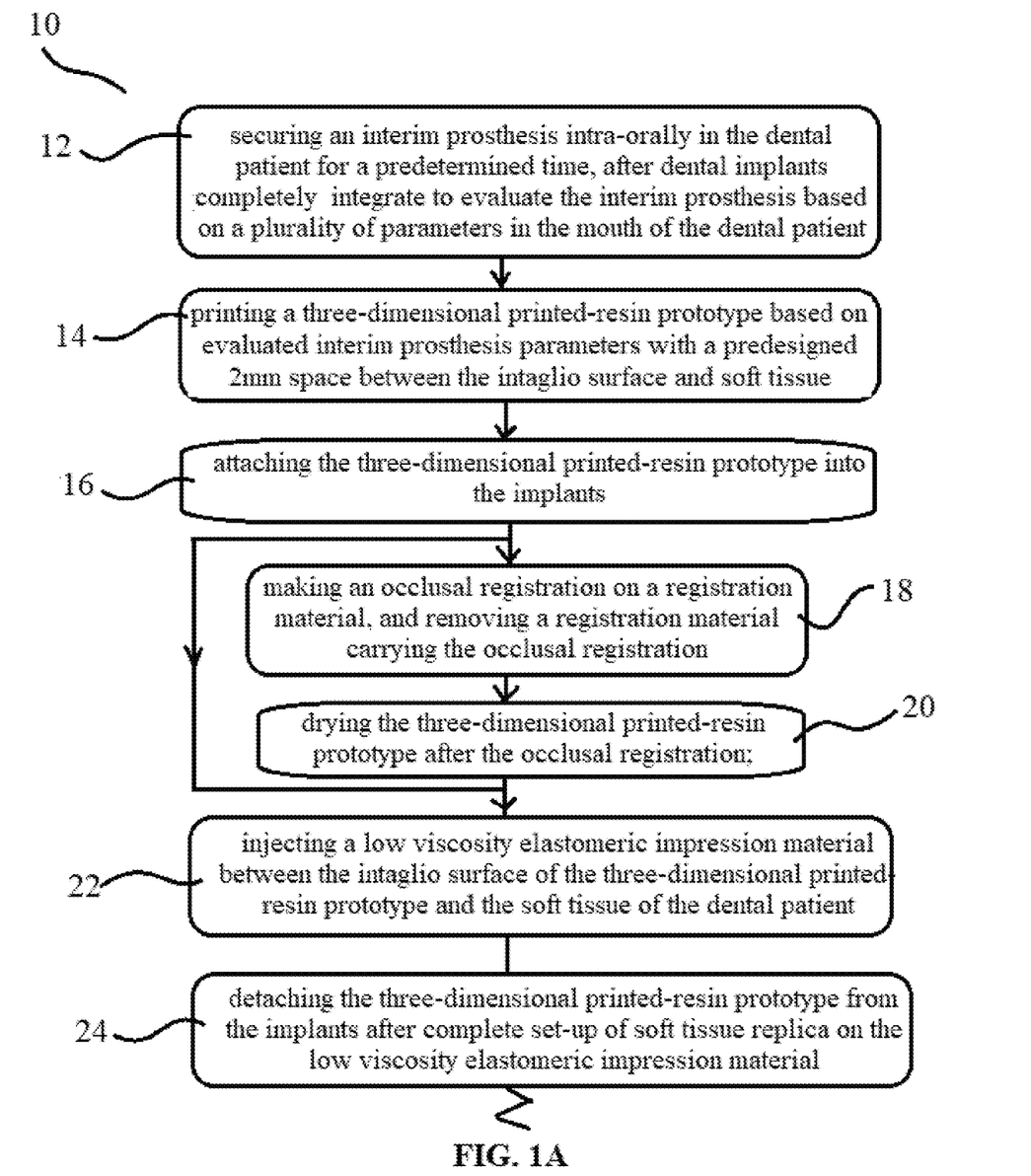
FIG. 1A illustrates a process for replicating soft tissue anatomy of a dental patient prior to preparing an implant-supported fixed prosthesis, in accordance with an exemplary embodiment of the present disclosure.
Figure 1B:
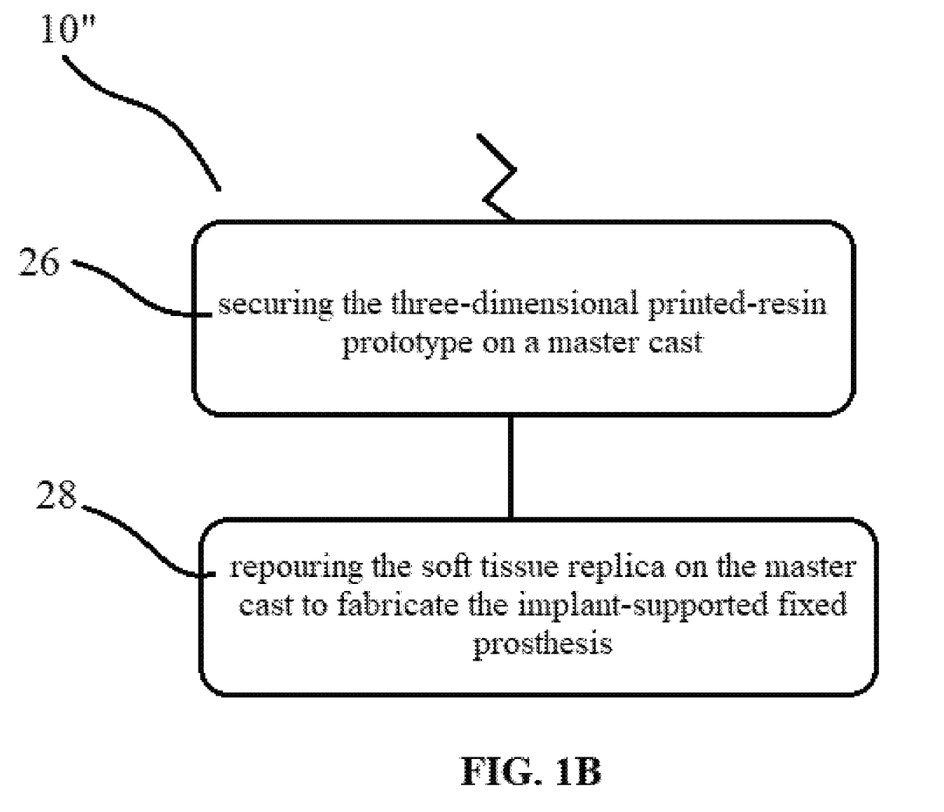
FIG. 1B illustrates a process that may be continuation to the process as seen in FIG. 1A, in accordance with an exemplary embodiment of the present disclosure.
Figure 10A:
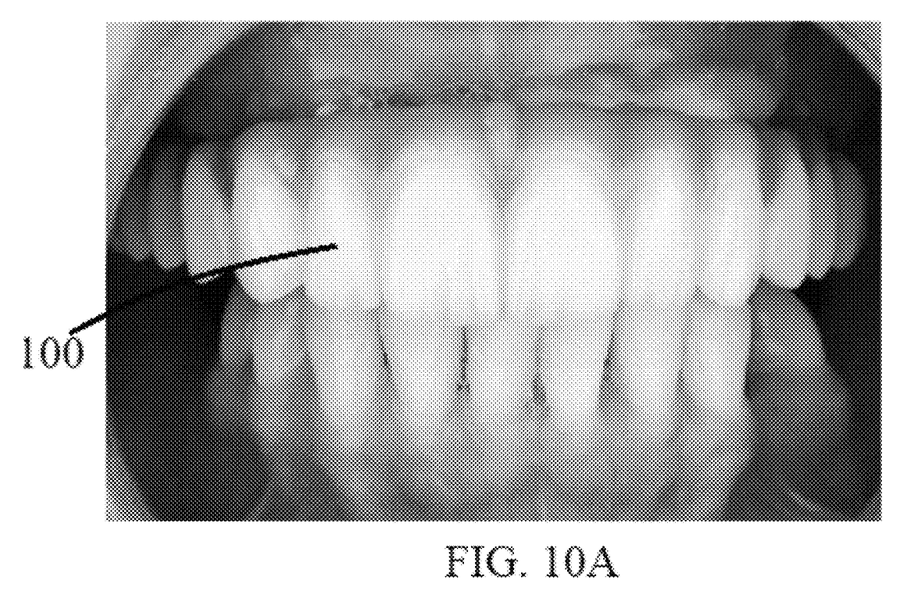
Figure 10B:
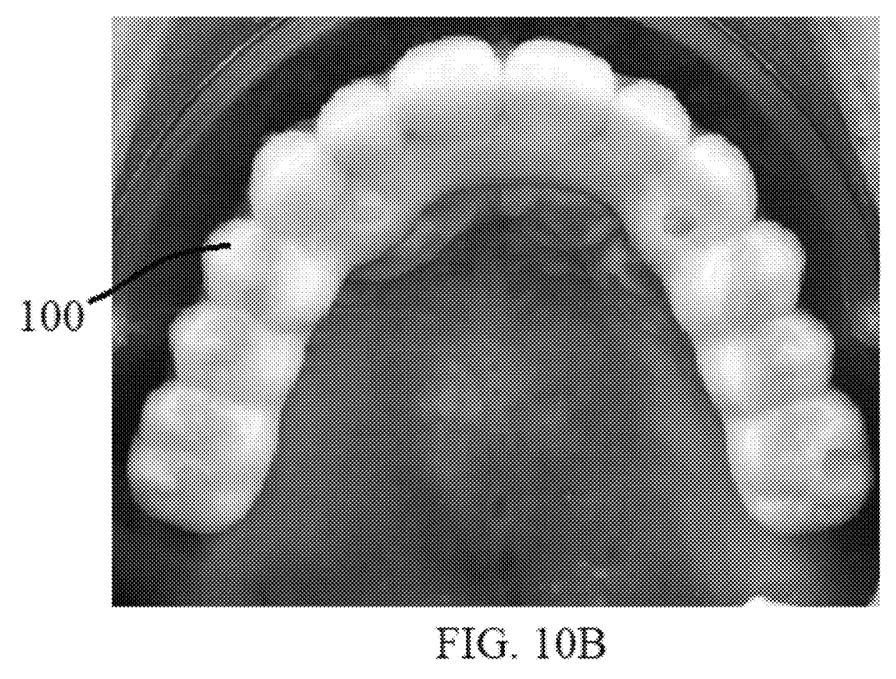
Figure 11:
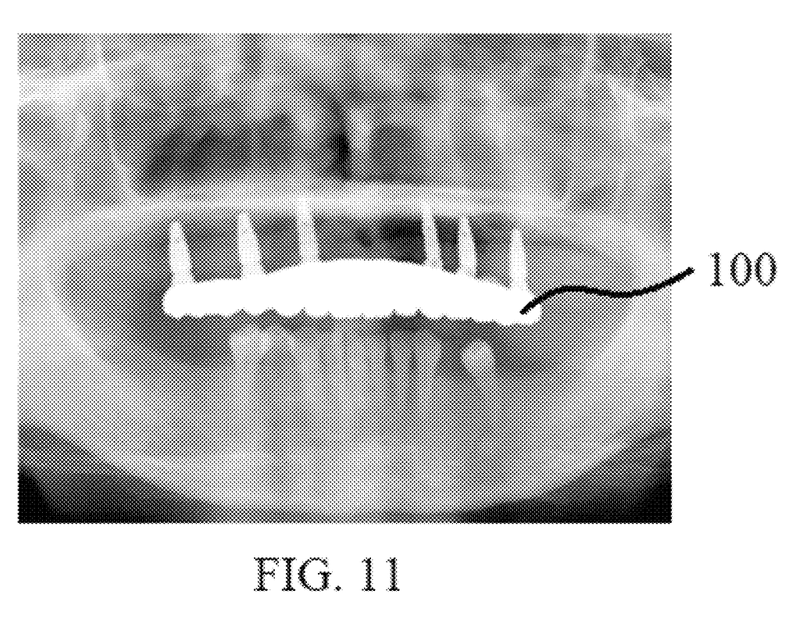
Figure 12:
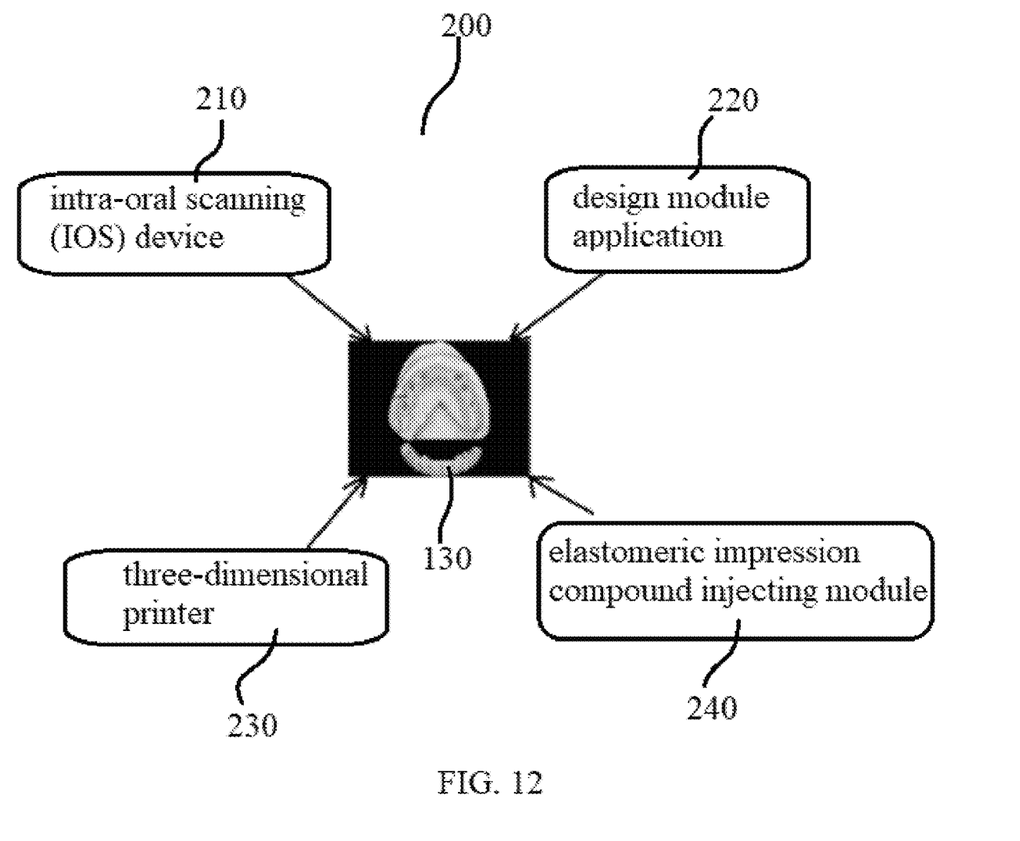
FIG. 12 illustrates the system that uses the process 10 and 10" for replicating soft tissue anatomy of a dental patient prior to preparing an implant-supported fixed prosthesis, in accordance with an exemplary embodiment of the present disclosure.

A process 10 and a system 200 will now be described in conjunction with FIGS. 1A to 12. FIG. 1A illustrates the process 10 for replicating soft tissue anatomy of a dental patient prior to preparing an implant-supported fixed prosthesis 100 (seen in FIGS. 12A and 12B). Further, FIG. 1B illustrates a process 10" that may be a continuation to the process 10 as seen in FIG. 1A. Further, FIGS. 2A to 11 illustrates various stages of the process 10 or 10". Furthermore, FIG. 12 illustrates the system 200 that uses the process 10 and 10" for replicating soft tissue anatomy of a dental patient prior to preparing an implant-supported fixed prosthesis 100.

Figure 2A:
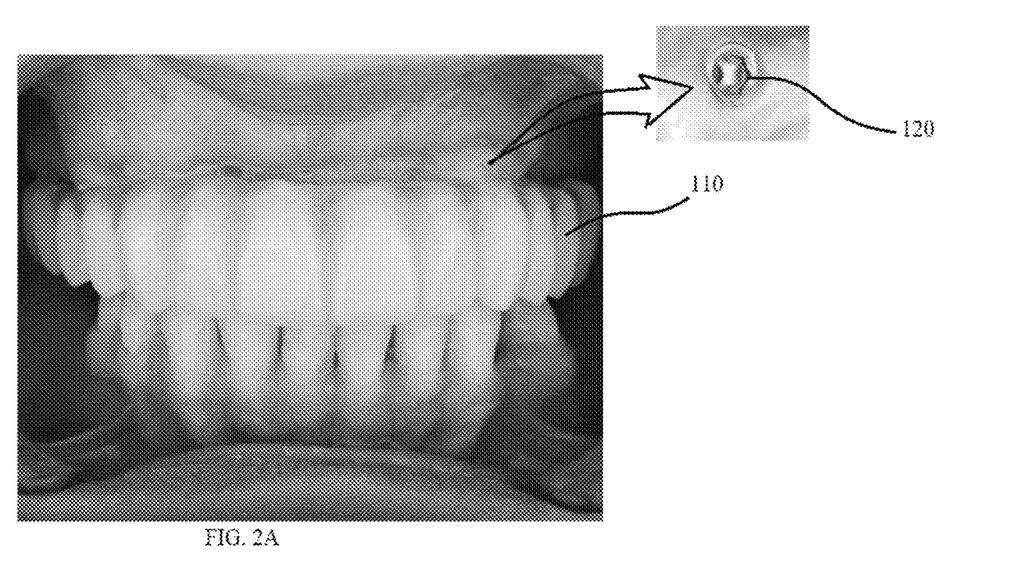
Figure 2B:
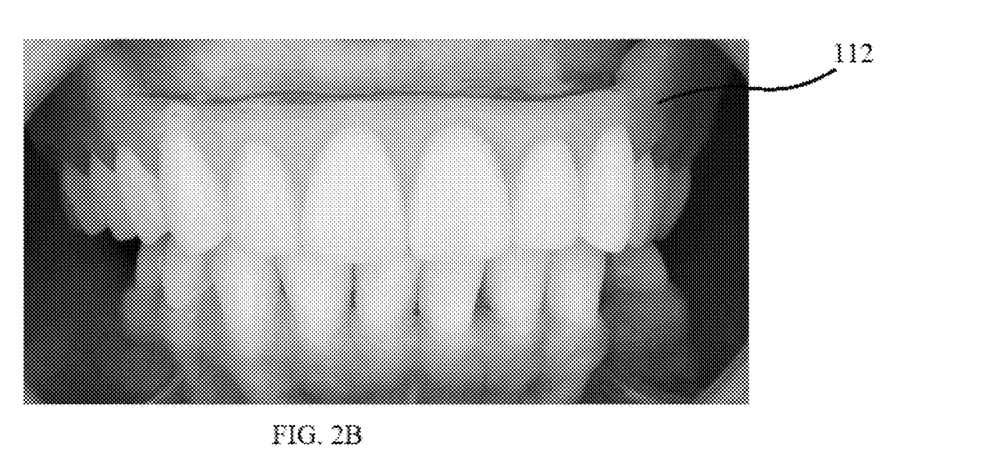

Referring now to FIG. 1A, the process 10, at step 12, may include securing an interim prosthesis 110 intra-orally in the dental patient for a predetermined time to evaluate the interim prosthesis 110 based on a plurality of parameters related to teeth and its alignment within the mouth of the dental patient. In an embodiment of the present step 12, as seen in FIG. 2A, when implants 120 in the mouth of the patient are osseointegrated, the interim prosthesis 110 is secured in the implants 120 being evaluated based on the plurality of parameters including, but not limited to, functional and aesthetic parameters including sufficient lip support, occlusal plane, and desired occlusal scheme of the dental patient. In certain embodiments, where the interim prosthesis 110 is not functionally and aesthetically appropriate in the mouth of the patient, in such embodiments a wax rim may be fabricated and arranged using a flangeless try-in 112, such as seen in FIG. 2B. Once the plurality of parameters on the interim prosthesis 110 or the wax rim are evaluated, the dentist may proceed to perform further steps required for preparing the implant-supported fixed prosthesis 100.

Figure 3A:
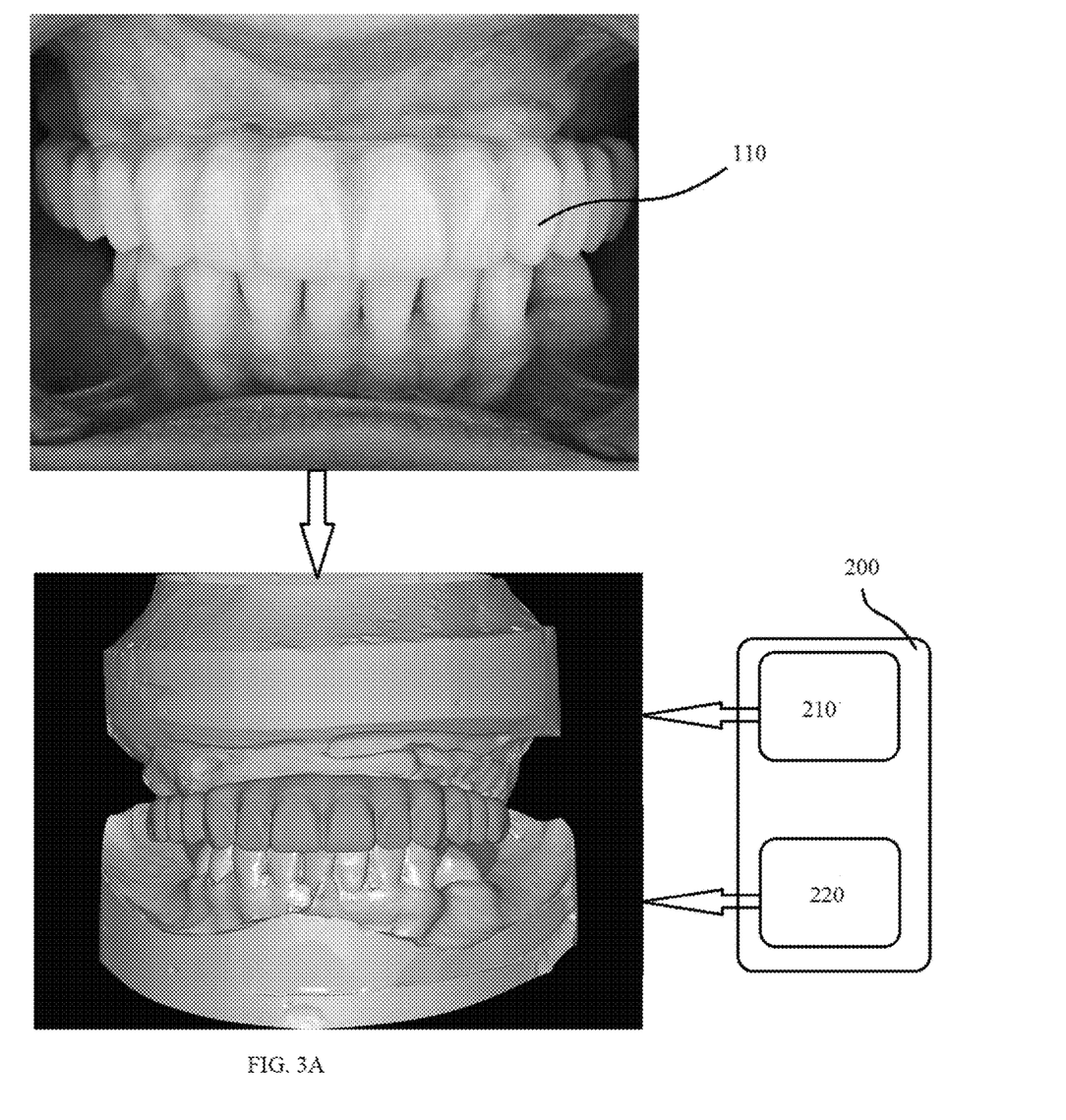
Figure 3B:
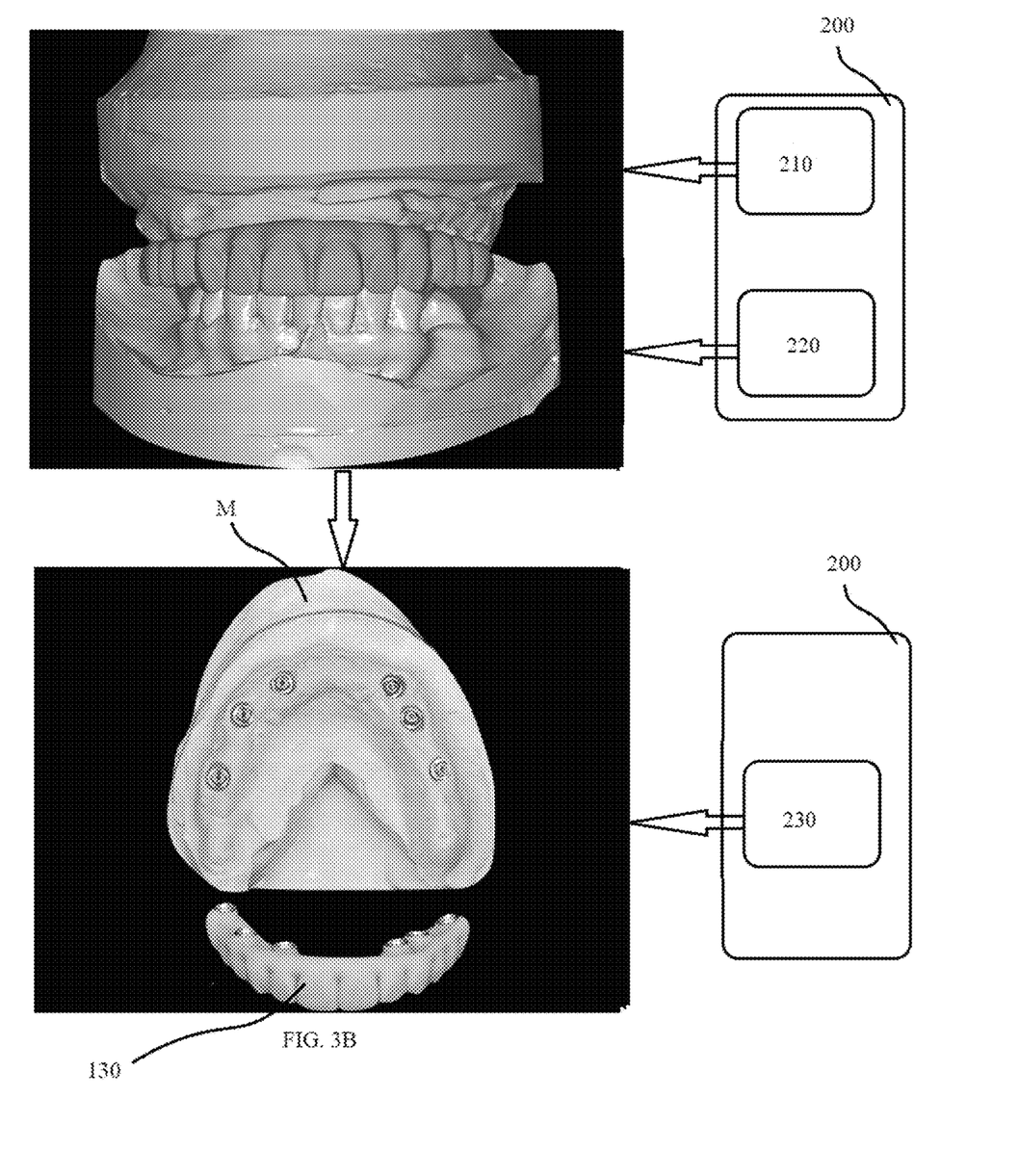

The process 10, at step 14, may include printing of a three-dimensional printed-resin prototype 130 (hereinafter may be referred to as "prototype 130") based on the evaluated interim prosthesis 110. The prototype 130 may define an intaglio surface 132. In an embodiment of the step 14, as seen in FIGS. 3A-3C will be described in conjunction to the system 200 as seen in FIG. 12. The prototype 130 is printed based on the evaluated interim prosthesis 100. Prior to printing, the prototype 130, in one embodiment, the intra-oral profile and along with the evaluated interim prosthesis 110 are scanned, via an intra-oral scanning (IOS) device 210, to digitize the intra-oral profile and along with the evaluated interim prosthesis 110, as seen in FIG. 3A. Once digitization of the intra-oral profile and along with the evaluated interim prosthesis 110 by the intra-oral scanning (IOS) device 210 is done, the prototype 130 with the intaglio surface 132 (seen in FIG. 4) having 2 millimeters (mm) cutback from the soft tissue (S) of the patient is designed via a design module application 220. Further, as seen in FIG. 3B, the designed prototype 130 may be printed, via a three-dimensional printer 230. FIG. 3B, specifically, depicts printed prototype 130 and a master cast (M) with a previous soft tissue replica. In one example FIG. 4, the prototype 130 may be depicted to include the intaglio surface 132 and at least one temporary non-engaging abutments 134, as will be described hereinbelow.

Figure 4:
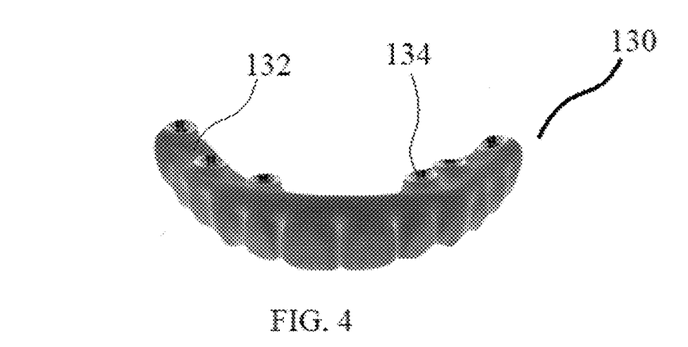
Figure 5:
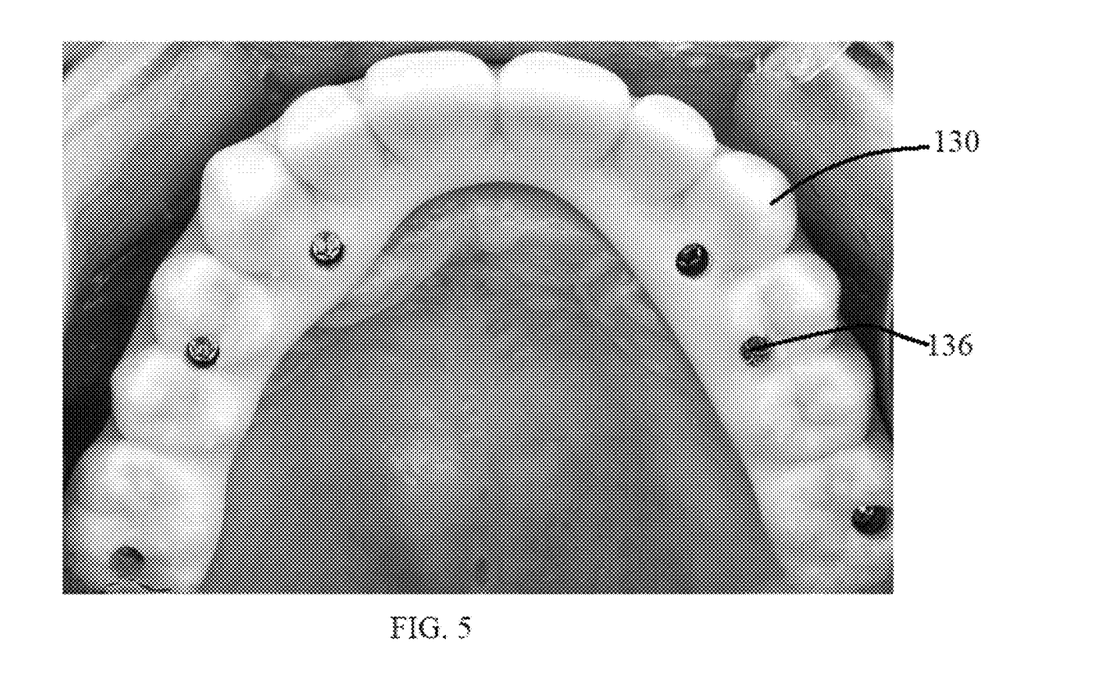
Figure 6A:
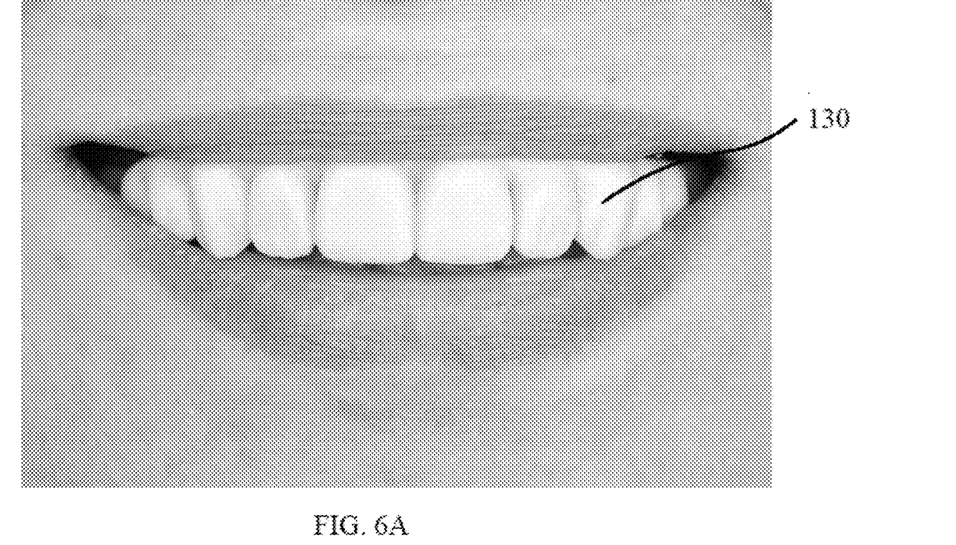
Figure 6B:
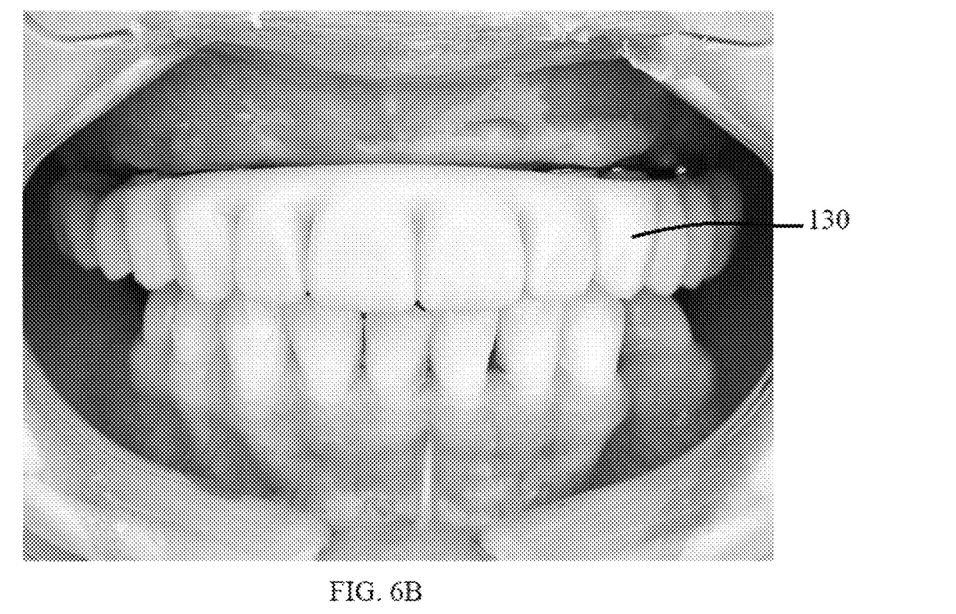

After step 14 the process 10, may include step 16, wherein the prototype 130 may be attached to the implants 120, as depicted in FIG. 5. In one embodiment of the present invention, the prototype 130 may include at least one temporary non-engaging abutment 136 (hereinafter referred to as "abutments" plural), as seen in FIG. 4. The abutments 134 may be complementary to the implants 120. To attach the prototype 130 to the implants 120, the at least one temporary non-engaging abutments 136 is removed and the prototype 130 is secured into the implants 120. In one example, confirmation of a passive seating of the prototype 130 may be first done using a 1-screw test, wherein only one screw 136 is secured in the implant. Upon confirmation, the remaining screws 136 may be secured in the implants 120. Once the prototype 130 is properly secured, the dentist may check extra-oral features, such as an incisal display at rest, tooth display on an extreme smile, lip support, phonetics, and general facial scaffolding, as seen in FIG. 6A. Furthermore, the dentist may also check intra-oral evaluation with prototype 130 in place, as seen in FIG. 6B.

In one example embodiment, the prototype 130 with the abutments 134 may be printed using the three-dimensional printer 1030, however, without departing from the scope of the present disclosure, the abutments 134 may be provided manually or secured via a machining tool.

The process 10, at step 22, may include injecting a low viscosity elastomeric impression material 140 (hereinafter may be referred to as "impression material 140") between the intaglio surface 132 of the prototype 130 and the soft tissue (S) of the dental patient to obtain a soft tissue replica 150 for preparing the implant-supported fixed prosthesis 100 and will be described herein in conjunction with FIGS. 8A-8D. In one embodiment, without departing from the scope of the present disclosure, the impression material 140 may be Poly-Vinyl Siloxane (PVC). The system 200, as seen in FIG. 12, may include an elastomeric impression compound injecting module 240 for injecting impression material 140.

Figure 7A:
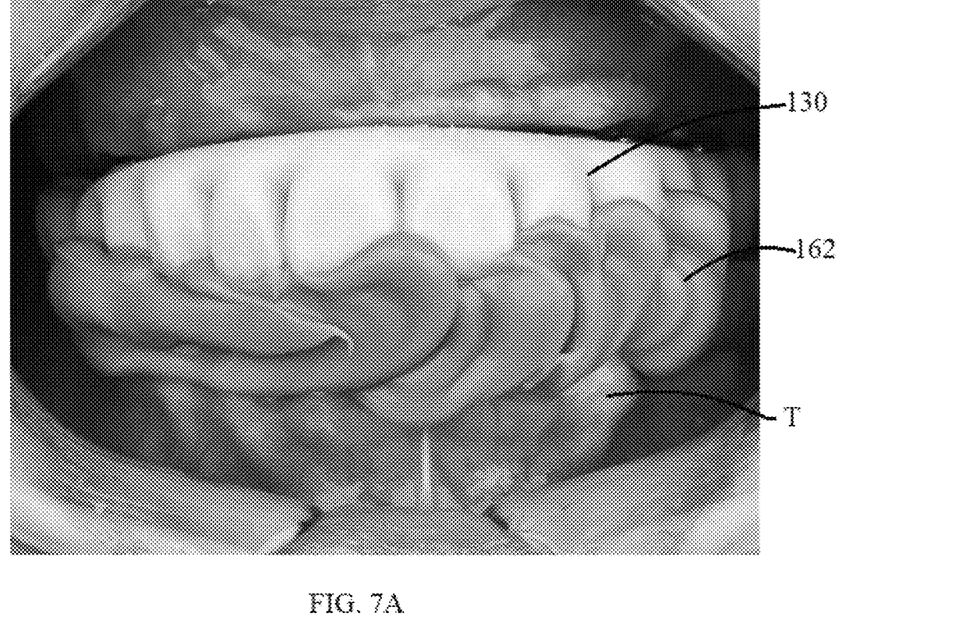
Figure 7B:
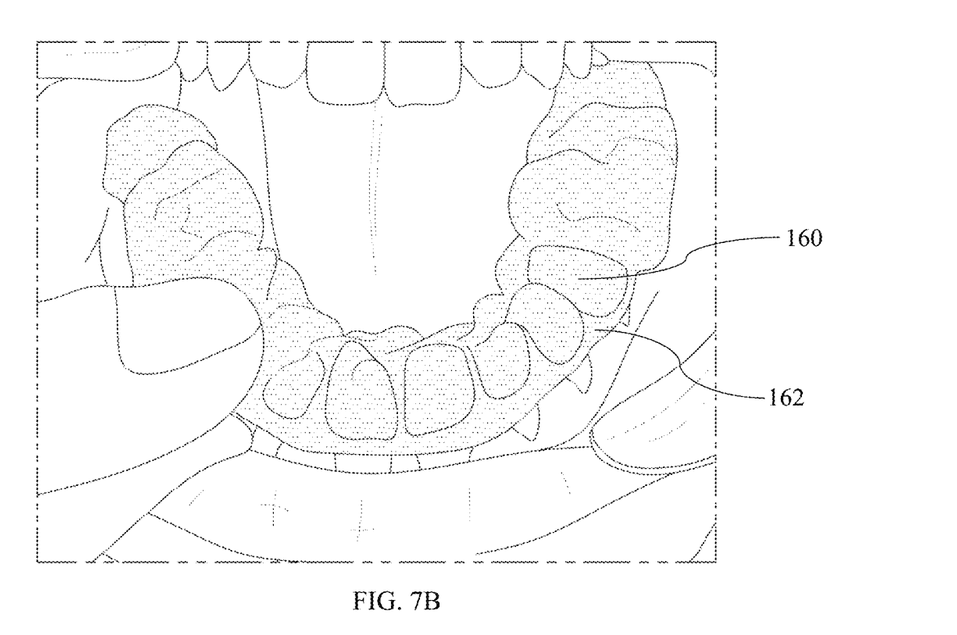

In one embodiment, the process 10, upon requirement, may include making an occlusal registration 160, prior to obtaining the soft tissue replica 150. For example, at step 18, of the process 10, the occlusal registration 160, as seen in FIGS. 7A and 7B, are made by placing the registration material 162 intra-orally in the dental patient, between the prototype 130 and apposing teeth or arches (T). Further, the registration material 162 is pressed by the dental patient between the prototype 130 and the apposing teeth or arches (T) to obtain the occlusal registration 160. Upon obtaining the occlusal registration 160 on the registration material 162, the registration material 162 carrying the occlusal registration 160 may be removed from the mouth of the dental patient after setting the occlusal registration 160.

In one further embodiment, once the occlusal registration 160 is removed from the mouth of the patient, the prototype 130 may be dried at step 20 of the process 10, prior to injecting the impression material 140 between the intaglio surface 132 of the prototype 130 and the soft tissue (S).

Figure 8A:
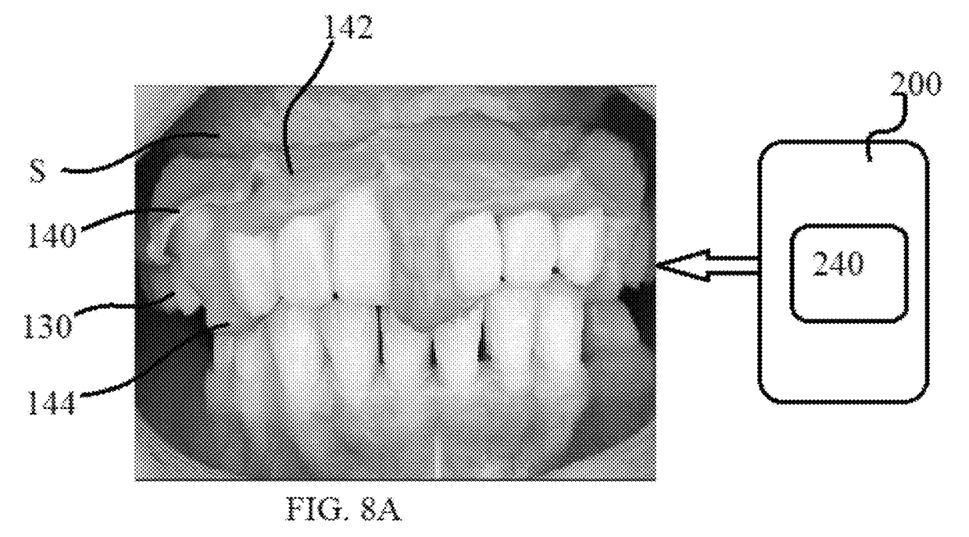
Figure 8B:
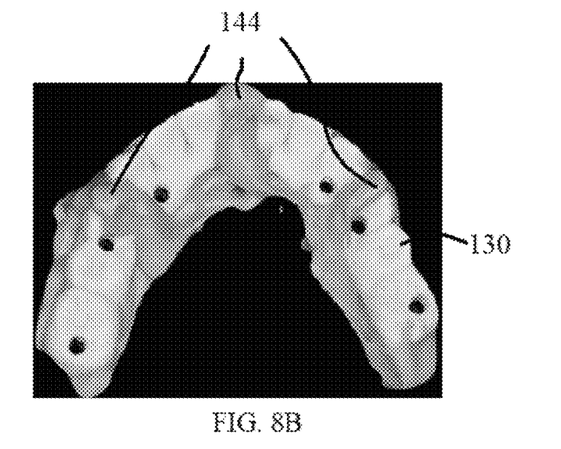
Figure 8C:
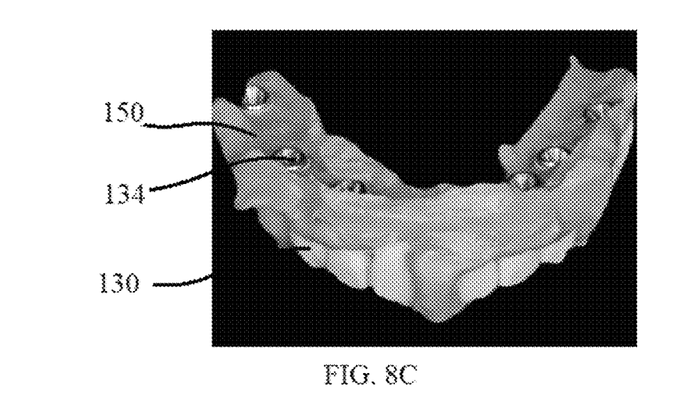
Figure 8D:
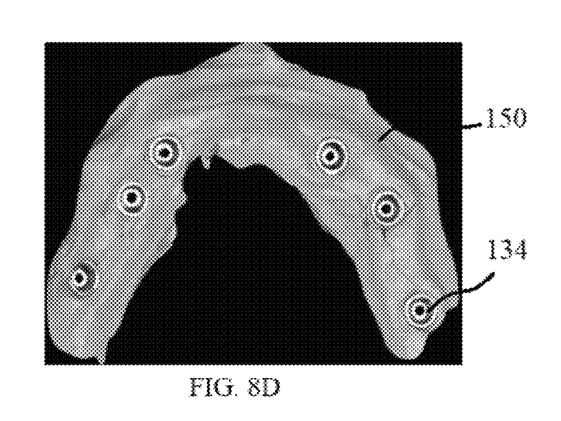

In one embodiment, as mentioned above, the step 22 of the process 10 of injecting the impression material 140 between the intaglio surface 132 of the prototype 130 and the soft tissue (S), firstly, includes injecting the impression material 140 between the intaglio surface 132 of the prototype 130 and the soft tissue (S) intra-orally in the patient, as indicated by numeral 142 seen in FIG. 8A. The impression material 140 may be injected starting from one side on the buccal all the way to the contralateral side and then around the distal end and alongside the palatal, to obtain the soft tissue replica 150. Thereafter, the impression material 140 may be wrapped around on at least one site of the prototype 130, as indicated by numeral 144 in FIGS. 8A and 8B. Such wrapping may stabilize the impression material 140 over the prototype 130, when the prototype 130 is detached from the mouth of the patient. In one example as seen in FIGS. 8A-8C, the impression material 140 may be wrapped around on three sites of the prototype 130 to stabilize the impression material 140 over the prototype 130.

Further, the process 10 may continue to include steps 24-28 depicted as a process 10" in FIG. 1B. Once the complete set-up of soft tissue replica 150 on the impression material 140 is obtained, the prototype 130 may be detached by unscrewing the screw(s) 136 from the implants 120 at step 24 of the process 10 for preparing the implant-supported fixed prosthesis 100. FIGS. 8A to 8C depict the detached prototype 130 with the soft tissue replica 150.

Figure 9A:
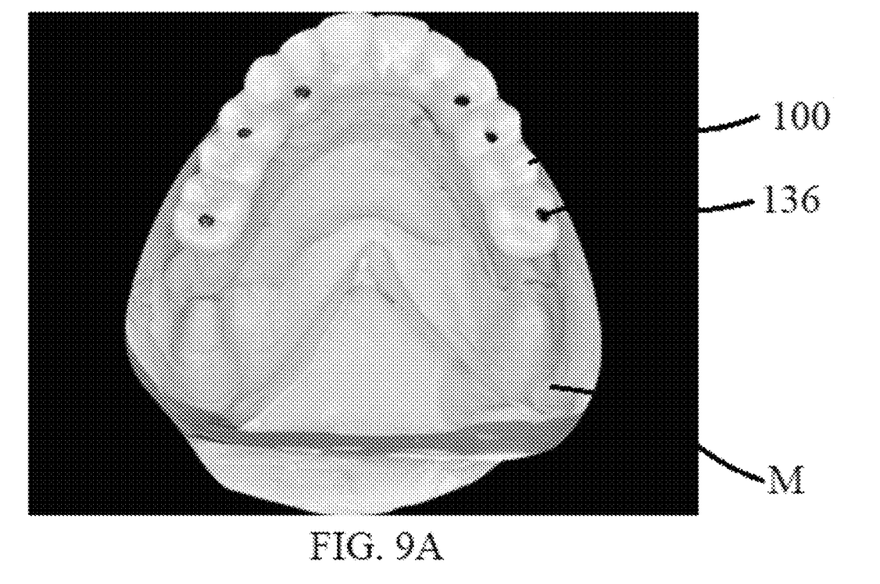
Figure 9B:
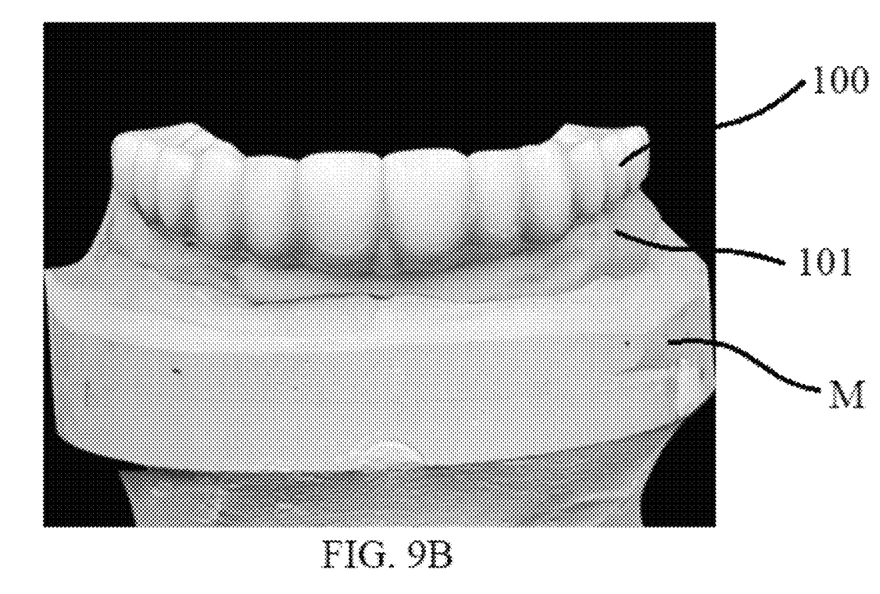

Further, when preparing the implant-supported fixed prosthesis 100, the prototype 140 as obtained at the step 24 may be secured on a master cast (M) using screws, such as screws 136 and complementary abutments of the master cast (M) at step 26 of the process 10, as seen in FIGS. 9A and 9B. Thereafter, at the step 28, the soft tissue replica 150 may be repoured on the master cast (M) allowing contours of the intaglio surface 132 and emergence profile to fabricate the implant-supported fixed prosthesis 100 based on the master cast (M). FIGS. 9A and 9B depict master cast (M) having new soft tissue analogue 101 and final implant-supported fixed prosthesis 100 to be delivered to be planted intra-orally in the patent as seen in FIGS. 10A and 10B. The delivered implant-supported fixed prosthesis 100 may be milled and include monolithic zirconia with incisors layered with lithium disilicate. A scanned view of the final implant-supported fixed prosthesis 100 fixed intra-orally is seen in FIG. 11.

Furthermore, FIG. 12 illustrates the system 200 that follows for replicating the soft tissue anatomy of a dental patient before preparing the implant-supported fixed prosthesis 100 with the help of processes 10 and 10", as described above and excluded herein from repetition for the sake of brevity.

The foregoing descriptions of specific embodiments of the present disclosure have been presented for purposes of illustration and description. They are not intended to be exhaustive or to limit the present disclosure to the precise forms disclosed, and many modifications and variations are possible in light of the above teaching. The embodiments were chosen and described to best explain the principles of the present disclosure and its practical application, and to thereby enable others skilled in the art to best utilize the present disclosure and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present disclosure.

What is claimed is:

1. A process for replicating soft tissue anatomy of a dental patient prior to preparing an implant-supported fixed prosthesis, the process comprising:
   securing an interim prosthesis intra-orally into integrated dental implants in the dental patient for a predetermined time, after the implants of the dental patient are osseointegrated, to evaluate the interim prosthesis based on a plurality of parameters within a mouth of the dental patient;
   printing a three-dimensional printed-resin prototype based on the evaluated interim prosthesis, the three-dimensional printed-resin prototype defining an intaglio surface with a predesigned 2 mm cutback between the intaglio surface and the soft tissue;
   attaching the three-dimensional printed-resin prototype into the implants; and
   injecting a low viscosity elastomeric impression material between the intaglio surface of the three-dimensional printed-resin prototype and the soft tissue of the dental patient to obtain a soft tissue replica for preparing the implant-supported fixed prosthesis.

2. The process as claimed in claim 1 wherein printing the three-dimensional printed-resin prototype based on the evaluated interim prosthesis comprises:
   scanning, via an intra-oral scanning (IOS) device, the evaluated interim prosthesis to digitize the evaluated interim prosthesis;
   designing, via a design module application, the three-dimensional printed-resin prototype with the intaglio surface having the 2 mm cutback from the soft tissue of the mouth of the dental patient, based on the digitized interim prosthesis; and
   printing, via a three-dimensional printer, the three-dimensional printed-resin prototype along with the intaglio surface with the 2 mm cutback from the soft tissue.

3. The process as claimed in claim 2, wherein the three-dimensional printed-resin prototype comprises:
   at least one temporary non-engaging abutments;
   wherein attaching the three-dimensional printed-resin prototype into the implants comprises:
   removing the at least one temporary non-engaging abutments and securing the prototype into the implants via at least one screw.

4. The process as claimed in claim 3 further comprising:
   detaching the at least one screw of the three-dimensional printed-resin prototype from the implants after a complete set-up of the soft tissue replica on the low viscosity elastomeric impression material for preparing the implant-supported fixed prosthesis.

5. The process as claimed in claim 4 further comprising:
   securing the three-dimensional printed-resin prototype on a master cast;
   repouring the soft tissue replica on the master cast allowing contours of the intaglio surface and emergence profile to fabricate the implant-supported fixed prosthesis based on the master cast.

6. The process as claimed in claim 1, wherein the injecting of the low viscosity elastomeric impression material between the intaglio surface of the three-dimensional printed-resin prototype and the soft tissue comprises:
   injecting the low viscosity elastomeric impression material between the intaglio surface of the three-dimensional printed-resin prototype and the soft tissue intra-orally in the patient, starting from one side on a buccal all the way to a contralateral side and then around a distal end and alongside a palatal, to obtain the soft tissue replica; and
   wrapping around the low viscosity elastomeric impression material on at least one site of the three-dimensional printed-resin prototype intra-orally in the dental patient to stabilize the low viscosity elastomeric impression material over the three-dimensional printed-resin prototype, after removal of the three-dimensional printed-resin prototype from the mouth of the patient.

7. The process as claimed in claim 1 further comprising:
   making an occlusal registration upon attaching the three-dimensional printed-resin prototype into the implants, prior to the injecting of the low viscosity elastomeric impression material between the intaglio surface of the three-dimensional printed-resin prototype and the soft tissue.

8. The process as claimed in claim 7, wherein making the occlusal registration comprises:
   placing a registration material intra-orally in the dental patient between the three-dimensional printed-resin prototype and apposing teeth or arches;
   obtaining the occlusal registration on the registration material; and
   removing the registration material carrying the occlusal registration from the mouth of the dental patient after setting the occlusal registration.

9. The process as claimed in claim 8 further comprising:
   drying the three-dimensional printed-resin prototype after the occlusal registration and prior to the injecting of the low viscosity elastomeric impression material between the intaglio surface of the three-dimensional printed-resin prototype and the soft tissue.

10. The process as claimed in claim 1, wherein the plurality of parameters comprises functional and esthetic parameters including sufficient lip support, occlusal plane, and desired occlusal scheme of the mouth of the dental patient.

11. The process as claimed in claim 1, wherein the low viscosity elastomeric impression material is Poly-Vinyl Siloxane (PVC).

12. An implant-supported fixed prosthesis prepared by the process as claimed in claim 1.

13. A process for replicating a soft tissue anatomy of a dental patient prior to preparing an implant-supported fixed prosthesis, the process comprising:
   securing an interim prosthesis intra-orally in the dental patient for a predetermined time, after implants of the dental patient are osseointegrated, to evaluate the interim prosthesis based on a plurality of parameters in a mouth of the dental patient;

printing a three-dimensional printed-resin prototype based on the evaluated interim prosthesis, the three-dimensional printed-resin prototype defining an intaglio surface;

attaching the three-dimensional printed-resin prototype into the implants;

making an occlusal registration on a registration material, upon attaching the three-dimensional printed-resin prototype into the implants, and removing the registration material carrying the occlusal registration from the mouth of the dental patient after setting off the occlusal registration;

drying the three-dimensional printed-resin prototype after the occlusal registration;

injecting a low viscosity elastomeric impression material between the intaglio surface of the three-dimensional printed-resin prototype and the soft tissue of the dental patient;

detaching the three-dimensional printed-resin prototype from the implants after a complete set-up of the soft tissue replica on the low viscosity elastomeric impression material;

securing the three-dimensional printed-resin prototype on a master cast;

repouring the soft tissue replica on the master cast allowing contours of the intaglio surface and emergence profile to fabricate the implant-supported fixed prosthesis based on the master cast.

14. The process as claimed in claim 13, wherein printing the three-dimensional printed-resin prototype based on the evaluated interim prosthesis comprises:

scanning the evaluated interim prosthesis using an intra-oral scanning (IOS) device to digitize the evaluated interim prosthesis on a design module application;

designing the intaglio surface with 2 millimeters (mm) cutback from the soft tissue for the three-dimensional printed-resin prototype on the design module application, based on the digitized interim prosthesis; and printing the three-dimensional printed-resin prototype along with the intaglio surface with the 2 mm cutback from soft tissue, using a three-dimensional printer.

15. The process as claimed in claim 14, wherein the three-dimensional printed-resin prototype comprises:

at least one temporary non-engaging abutments;

wherein attaching the three-dimensional printed-resin prototype into the implants comprises:

removing the at least one temporary non-engaging abutments and securing the prototype into the implants via at least one screw.

16. The process as claimed in claim 15 further comprising:

detaching the at least one screw from the three-dimensional printed-resin prototype from the implants after the complete set-up of soft tissue replica on the low viscosity elastomeric impression material for preparing the implant-supported fixed prosthesis.

17. The process as claimed in claim 13, wherein the injecting of the low viscosity elastomeric impression material between the intaglio surface of the three-dimensional printed-resin prototype and the soft tissue comprises:

the injecting of the low viscosity elastomeric impression material intra-orally in the dental patient between the intaglio surface of the three-dimensional printed-resin prototype and the soft tissue, starting from one side on a buccal all the way to a contralateral side and then around a distal end and alongside a palatal, to obtain the soft tissue replica; and wrapping around the low elastomeric impression material intra-orally in the dental patient on at least one site of the three-dimensional printed-resin prototype in the mouth of the dental patient to stabilize the low viscosity elastomeric impression material over the three-dimensional printed-resin prototype, after removal of the three-dimensional printed-resin prototype from the mouth of the dental patient.

18. The process as claimed in claim 13, wherein making the occlusal registration comprises:

placing the registration material intra-orally in the dental patient between the three-dimensional printed-resin prototype and apposing teeth or arches;

obtaining the occlusal registration on the registration material; and removing the registration material carrying the occlusal registration from the mouth of the dental patient after setting off the occlusal registration.

19. A system for preparing an implant-supported fixed prosthesis for a dental patient, the system comprising:

an intra-oral scanning (IOS) device to scan an interim prosthesis to digitize the interim prosthesis, wherein the interim prosthesis is evaluated based on a plurality of parameters configured to be in a mouth of the dental patient placed for a predetermined time, after implants of the dental patient are osseointegrated;

a design module application to design a three-dimensional printed-resin prototype with an intaglio surface having 2 millimeters (mm) cutback from the soft tissue of the mouth of the dental patient, based on the digitized interim prosthesis;

a three-dimensional printer to print the three-dimensional printed-resin prototype along with the intaglio surface with the 2 mm cutback configured to be from the soft tissue; and an elastomeric impression compound injecting module to inject a low viscosity elastomeric impression material between the intaglio surface of the three-dimensional printed-resin prototype and the soft tissue in the mouth of the dental patient to obtain a soft tissue replica of the dental patient to prepare the implant-supported fixed prosthesis.

20. The system as claimed in claim 19, wherein injecting the low viscosity elastomeric impression material, via the elastomeric impression compound injecting module, between the intaglio surface of the three-dimensional printed-resin prototype and the soft tissue, comprises a system:

configured to inject the low viscosity elastomeric impression material intra-orally in the dental patient between the intaglio surface of the three-dimensional printed-resin prototype and the soft tissue, starting from one side on the buccal all the way to the contralateral side and then around the distal end and alongside the palatal, to obtain the soft tissue replica; and configured to wrap around the low elastomeric impression material intra-orally in the dental patient on at least one site of the three-dimensional printed-resin prototype in the mouth of the dental patient to stabilize the low viscosity elastomeric impression material over the three-dimensional printed-resin prototype, after removal of the three-dimensional printed-resin prototype from the mouth of the dental patient.

* * * * *